US00PP21893P2

(12) United States Plant Patent
Hurd

(10) Patent No.: US PP21,893 P2
(45) Date of Patent: May 3, 2011

(54) ***DIANTHUS* PLANT NAMED 'BLACK CHERRY WILD'**

(50) Latin Name: *Dianthus hybrid*
Varietal Denomination: Black Cherry Wild

(75) Inventor: Kevin Hurd, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 12/462,742

(22) Filed: Aug. 7, 2009

(51) Int. Cl.
*A01H 5/00* (2006.01)

(52) U.S. Cl. ..... Plt./272

(58) Field of Classification Search ..... Plt./272
See application file for complete search history.

*Primary Examiner* — Susan B McCormick Ewoldt

(57) ABSTRACT

The new and distinct cultivar of perennial Carnation or Pinks, *Dianthus* plant named 'Black Cherry Wild' with long-blooming, highly double flowers with fragrant highly double flowers, petals with a deep crimson outer surface surrounded on the outside by a lighter rose pink perimeter. *Dianthus* 'Black Cherry Wild' is tolerant of high temperatures and resists center dying out.

2 Drawing Sheets

Botanical denomination: *Dianthus* hybrid.
Cultivar designation: 'Black Cherry Wild'.

BACKGROUND OF THE INVENTION

The present invention relates to the new and distinct cultivar of *Dianthus* or Pinks from the genus *Dianthus* and given the cultivar name 'Black Cherry Wild'. The new plant was the result of an intentional cross in May of 2006 by Kevin A. Hurd between 'Double Spotty' U.S. Plant Pat. No. 13,884 as the seed parent and 'Red Dwarf' U.S. Plant Pat. No. 14,437 (more often known as 'Eastern Star') as the pollen parent. The new hybrid was first isolated from trials at a nursery in Zeeland, Mich. during the summer of 2007. *Dianthus* 'Black Cherry Wild' has been asexually propagated at the same nursery in Zeeland, Mich. using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Double flowers with high petal counts.
2. High heat tolerance.
3. Floriferous habit.
4. Vigorous growth and excellent habit.
5. Compact, distinctly blue-green foliage.

Table of Dianthus Comparisons

| Cultivar | Flower color | Flower pattern | Flower size |
|---|---|---|---|
| 'Apple Slice' application No. 12/462,743 | pink | dark wine edge and rim | 4.5 cm |

-continued

Table of Dianthus Comparisons

| | | | |
|---|---|---|---|
| 'Black Cherry Wild' application No. 12/462,742 | burgundy | solid | 4.0 cm |
| 'Coconut Punch' application No. 12/462,744 | white | burgundy edge with white rim | 3.5 cm |
| 'Double Spotty' U.S. Plant Pat. No. 13,884 | burgundy | white picotee edge and white spots | 4.0 cm |
| 'Dragon Fruit' application No. 12/462,745 | fuchsia pink | red jagged purple bar | 3.5 cm |
| 'Pomegranate Kiss' application No. 12/462,746 | burgundy | Irregular pink splashing on margin or center | 3.2 cm |
| 'Cranberry Ice' U.S. Plant Pat. No. 18,342 | pink | dark wine edge and rim | 3.3 cm |
| 'Devon Siskin' U.S. Plant Pat. No. 14,377 | light pink | magenta edge with burgundy base | 4.0 cm |
| 'Feuerhexe' (not patented) | pink | solid | |
| 'Devon Xera' U.S. Plant Pat. No. 14,895 | red | crimson eye | 3.0 cm |
| Red Dwarf' U.S. Plant Pat. No. 14,437 | red | crimson eye | 3.5 cm |
| 'Sangria Splash' application No. 12/462,741 | fuchsia pink | crimson ring with pink splashing and center | 3.0 cm |
| 'Spangled Star' U.S. Plant Pat. No. 13,029 | scarlet red | small white spots and white picotee edge | 4.0 cm |

| Cultivar | Petal margin | Petal # | Plant height in flower |
|---|---|---|---|
| 'Apple Slice' application No. 12/462,743 | dark wine margin | 20 to 24 | 22 cm |
| 'Black Cherry Wild' | light rose | 16 to | 22 cm |

-continued

Table of Dianthus Comparisons

| | | | |
|---|---|---|---|
| application No. 12/462,742 | margin | 20 | |
| 'Coconut Punch' application No. 12/462,744 | reddish purple margin | 14 to 30 | 28 cm |
| 'Double Spotty' U.S. Plant Pat. No. 13,884 | white | 15 to 20 | 17 to 30 cm |
| 'Dragon Fruit' application No. 12/462,745 | self | 14 to 22 | 20 cm |
| 'Pomegranate Kiss' application No. 12/462,746 | irregular pink splashing | 16 to 22 | 16 cm |
| 'Cranberry Ice' U.S. Plant Pat. No. 18,342 | dark wine margin | 5 | 20 to 25 cm |
| 'Devon Siskin' U.S. Plant Pat. No. 14,377 | magenta edge | 5 | 10 cm |
| 'Feuerhexe' (not patented) | self | 5 | 10 to 12 cm |
| 'Devon Xera' U.S. Plant Pat. No. 14,895 | self | 5 | 15 to 20 cm |
| Red Dwarf' U.S. Plant Pat. No. 14,437 | self | 5 | 20 to 25 cm |
| 'Sangria Splash' application No. 12/462,741 | crimson with pink splashing | 5 | 30 cm |
| 'Spangled Star' U.S. Plant Pat. No. 13,029 | white picotee edge | 5 | 17 to 22 cm |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
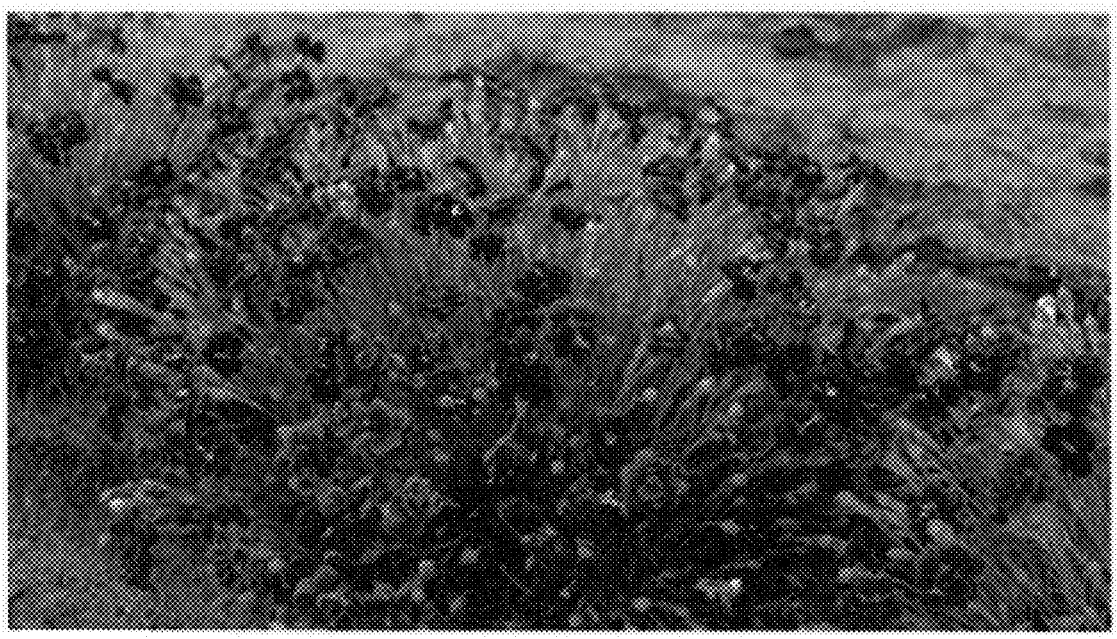
FIG. 1 shows a two-year old new plant in flower.
Figure 2:
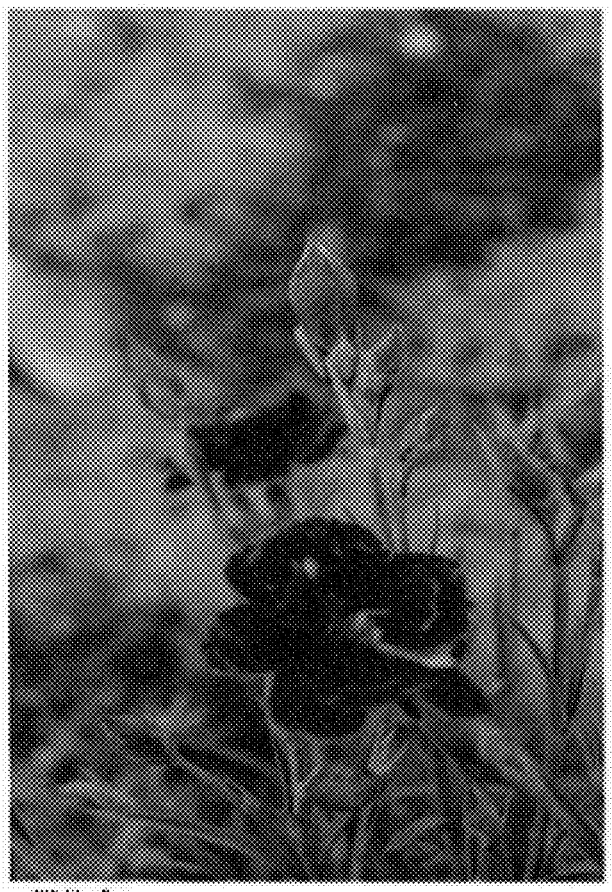
FIG. 2 shows a close-up of the flower and bud.
Figure 3:
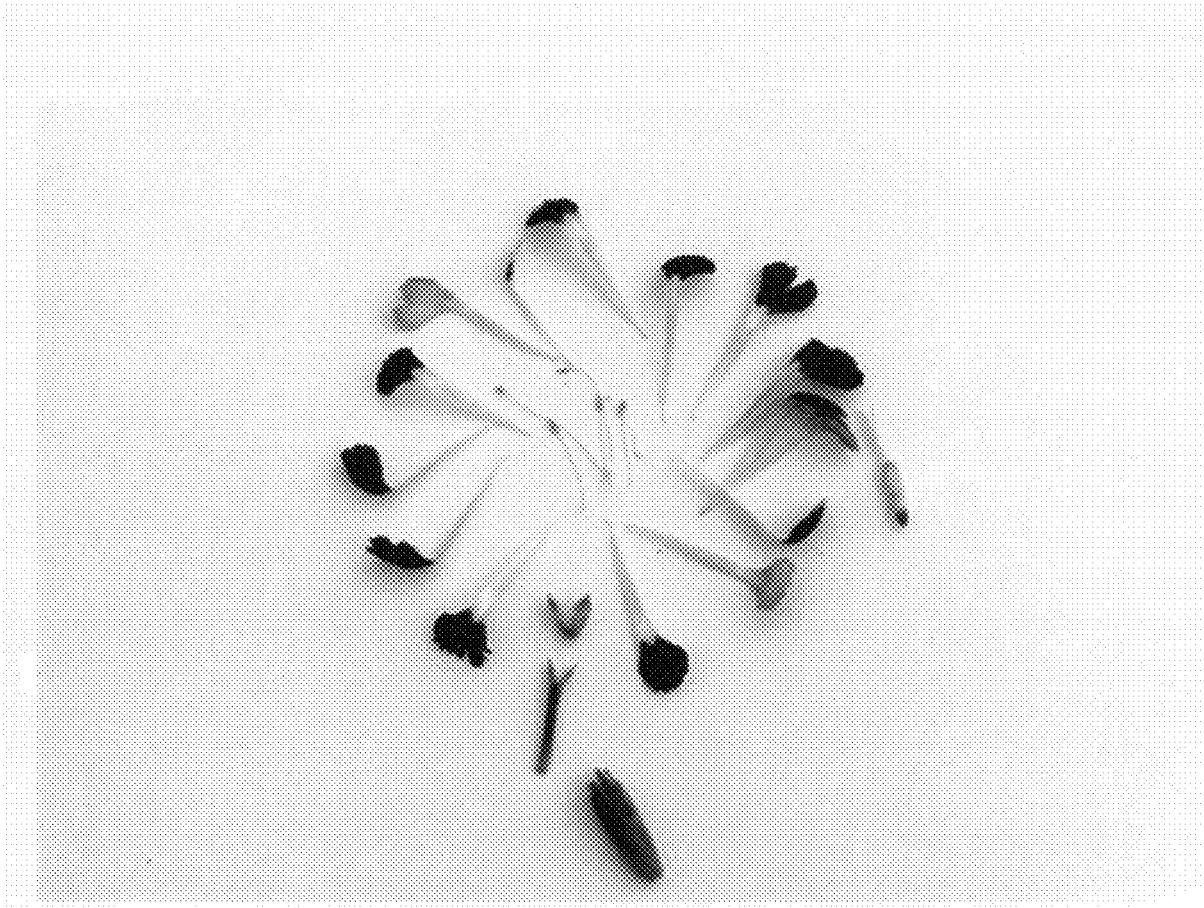
FIG. 3 shows the dissected flower of the new plant together with capsule and seeds.

The following detailed description of the new plant is based on observations of two-year old plants in open-field, full-sun conditions in Zeeland, Mich. with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid;

Parentage: 'Double Spotty' (female) times 'Eastern Star' (male);

Plant description:

*Habit.*—Cespitose, herbaceous, evergreen perennial; stems proximally branched, erect; height of foliage about 15 cm and 28 cm across; height in flower about 22 cm; Root system; fibrous.

Foliage:

*Leaf type.*—Simple, linear, opposite, decussate, sessile, glabrous, glaucous on adaxial and adaxial; acute apex; base decurrent, adpressed along stem and somewhat perfoliate; no fragrance detected.

*Leaf dimensions.*—About 5 cm long and 3 mm wide.

*Leaf color.*—Nearest RHS 122A adaxial and abaxial sides.

*Venation.*—Finely reticulate, coloration same as that of leaf top and bottom.

*Stems.*—Erect to arching, terete, glabrous, glaucous, proximally branching at 2 to 3 nodes.

*Stem size.*—About 22 cm long and 3 mm wide at base.

*Stem color.*—Nearest RHS 122A.

*Branching.*—Numerous from lower leaf axils; about 130 per plant.

*Nodes.*—4 mm across, RHS N134A.

*Internodes.*—4 to 4.5 cm apart.

Inflorescence:

*Type.*—Terminal, cymose, erect.

*Flowers per stem.*—Usually 3 to 4.

Flowers:

*Type.*—Salviform, completely double, symmetrical.

*Dimension.*—3.5 cm to 4.0 cm across and extending 1.7 cm above calyx.

*Flower bud shape.*—Rhomboid to terete.

*Flower bud size one day prior to opening.*—About 2 cm long and 1 cm wide.

*Flower bud color.*—Glaucous, more gray than RHS N138C and without anthocyanin patches.

*Flower period.*—Starting early June and after a 2 week rest continuing until frost.

*Flower lasting quality.*—About one week on or off the plant.

*Flower fragrance.*—Light, distinctly spicy, clove-like.

*Petals.*—16 to 20, consisting of a rounded blade or limb and a claw (enclosed completely within the calyx), obovate, apex dentate with dentations 3 to 4 mm deep, bearded with minute hairs mostly on the center of the adaxial surface, bent outwardly to nearly a ninety degree angle; dark wine-colored on adaxial side about 5 mm thick.

*Dimension.*—Variable, to 3.2 cm long including claw and limb; larger petal limb to 1.2 cm across and 1.0 cm long, smaller limbs to 3 mm across and 5 mm long; claws range from 1.7 cm to 2.4 cm long and 2 mm to 4 mm wide about 3 mm from limb.

*Color.*—Adaxial limb: RHS N79A with a 3 to 4 mm portion on both surfaces bleeding into the claw region of RHS N66D, with a lighter rose color nearest RHS 65B around the perimeter; abaxial limb: (showing through from adaxial side) closest to RHS 73D; claw: between RHS 145B and RHS 145C both sides.

*Calyx.*—Glabrous, glaucous, five-toothed corolla tube fused in proximal 1.0 cm; about 1.8 cm long and 0.7 cm in diameter; RHS 147D with anthocyanin tinting between RHS 187B and RHS N187B.

*Peduncle.*—Glabrous, glaucous, terete, 22 cm long and 2 mm diameter; RHS N138D.

*Bracts.*—Two, opposite, broadly obtuse with acute apex, about8 mm long and 7.5 mm wide; RHS N138C in the center, lighter than RHS 138D at base and margins.

*Bracteoles.*—Two, opposite, broadly obtuse with acute apex, bases joined at stem; about 6 mm long and 4 mm wide; glaucous, RHS N138C at apex and center, lighter than RHS 138D at base and margins.

*Stipules.*—None present.

*Androecium.*—Stamens 6, filaments variable in length from 1.2 to 1.8 cm long, less than 1 mm diameter; pale green lighter than RHS 11D; anther oblong to 2.2 mm long and 1 mm wide, RHS164B; pollen rare, pollen color RHS 11D.

*Gynoecium.*—Style split in two above ovary, pistil 2 cm long and about 1 mm diameter, lighter than RHS 11D except for distal 5 mm which are lighter than RHS 77D; stigma between RHS 77C and RHS 77B.

*Ovary.*—Superior, spindle-shaped; 8 mm long and 3 mm wide; nearest RHS 145C throughout.

Seed: Seeds have not been observed;

Growth rate: Vigorous, finishing from a 3 cm liner into a 15 cm in 6 to 8 weeks;

Comparison varieties: In comparison to the two parents, the new plant has a double, darker crimson petals with a fine lighter pink edge emerging, and 'Eastern Star' has single lighter red flowers with a darker red eye. *Dianthus* 'Double Spotty' has double flowers, but the petals are much lighter and have large spots of near light pink. The nearest know cultivar is 'Valda Kitty' U.S. Plant Pat. No. 13,872 which has lighter red adaxial petal surfaces and dark red abaxial surfaces with no fragrance to the flower.

Disease resistance: The new plant is resistant to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct cultivar of perennial Carnation or Pinks, *Dianthus* plant named 'Black Cherry Wild' as herein described and illustrated, with fragrant highly double flowers, petals with a deep crimson outer surface surrounded on the outside by a lighter rose pink perimeter, tolerant of high temperatures, resistant to center die out, and suitable as a garden ornamental, potted plant and for cut flower arrangements.

* * * * *